United States Patent
He et al.

(10) Patent No.: US 9,643,978 B2
(45) Date of Patent: May 9, 2017

(54) METHODS AND COMPOUNDS FOR SYNTHESIZING FUSED THIOPHENES

(71) Applicant: Corning Incorporated, Corning, NY (US)

(72) Inventors: Mingqian He, Horseheads, NY (US); Weijun Niu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/133,668

(22) Filed: Apr. 20, 2016

(65) Prior Publication Data

US 2016/0318949 A1    Nov. 3, 2016

Related U.S. Application Data

(60) Provisional application No. 62/154,329, filed on Apr. 29, 2015.

(51) Int. Cl.

| | | |
|---|---|---|
| *C07D 495/22* | (2006.01) | |
| *C07D 333/22* | (2006.01) | |
| *C07D 495/04* | (2006.01) | |
| *C07D 333/34* | (2006.01) | |
| *C07F 9/6553* | (2006.01) | |
| *C07F 9/6561* | (2006.01) | |

(52) U.S. Cl.
CPC .......... *C07D 495/22* (2013.01); *C07D 333/22* (2013.01); *C07D 333/34* (2013.01); *C07D 495/04* (2013.01); *C07F 9/6561* (2013.01); *C07F 9/655345* (2013.01)

(58) Field of Classification Search
None
See application file for complete search history.

(56) References Cited

U.S. PATENT DOCUMENTS

| | | |
|---|---|---|
| 7,705,108 B2 | 4/2010 | He |
| 7,714,098 B2 | 5/2010 | Heeney et al. |
| 7,838,623 B2 | 11/2010 | He |
| 7,893,191 B2 | 2/2011 | He |
| 8,217,183 B2 | 7/2012 | He et al. |
| 8,278,346 B2 | 10/2012 | He et al. |
| 8,278,410 B2 | 10/2012 | He et al. |
| 8,349,998 B2 | 1/2013 | He |
| 8,389,669 B2 | 3/2013 | He |
| 8,487,114 B2 | 7/2013 | He et al. |
| 8,575,354 B1 | 11/2013 | He et al. |
| 8,846,855 B2 | 9/2014 | He et al. |
| 2011/0288306 A1 | 11/2011 | He et al. |
| 2013/0085256 A1 | 4/2013 | He et al. |
| 2013/0109821 A1 | 5/2013 | He et al. |

OTHER PUBLICATIONS

Mingqian He and Feixia Zhang: 11 Synthesis and Structure of Alkyl-Substituted Fused Thiophenes Containing up to Seven Rings, The Journal of Organic Chemistry, American Chemical Society, US, vol. 72, No. 2, Jan. 19, 2007 (Jan. 19, 2007), pp. 442-451, XP008139264, ISSN: 0022-3263, DOI: 10.1021/J0061853Y.
Shneider J. A. et al.: Tuning the electronic properties of poly(thienothiophene vinylene)s via alkylsulfanyl and alkylsulfonyl substituents 11, Macromolecules, vol. 46, Nov. 25, 2013 (Nov. 25, 2013), pp. 9231-9239.
International Search Report and Written Opinion PCT/US2016/028733 Dated Jun. 8, 2016.
Baurle et al. "Synthesis and Properties of a Series of Methyltio Oligothiophenes," Liebigs Ann., pp. 279-284 (1996).

*Primary Examiner* — Heidi Reese

(57) ABSTRACT

Disclosed herein are thiophene compounds of formulae (I), (I'), (II), (II'), (II''), and (II'''), methods for making such compounds, and methods for making β-R-substituted fused thiophene compounds by coupling such compounds.

21 Claims, 7 Drawing Sheets

METHODS AND COMPOUNDS FOR SYNTHESIZING FUSED THIOPHENES

This application claims the benefit of priority under 35 U.S.C. §119 of U.S. Provisional Application Ser. No. 62/154,329 filed on Apr. 29, 2015 the content of which is relied upon and incorporated herein by reference in its entirety.

FIELD OF THE DISCLOSURE

The disclosure relates generally to methods and compounds for making fused thiophene compounds, and more particularly to intermediate thiophene compounds, methods for making such compounds, and their use in forming β-R-substituted fused thiophene compounds.

BACKGROUND

Highly conjugated organic materials have been the focus of great research activity, chiefly due to their interesting electronic and optoelectronic properties. They have been investigated for use in a variety of applications, including field effect transistors (FETs), thin-film transistors (TFTs), organic light-emitting diodes (OLEDs), electro-optic (EO) applications, as conductive materials, as two photon mixing materials, as organic semiconductors, and as non-linear optical (NLO) materials. Highly conjugated organic materials may find utility in devices such as RFID tags, electroluminescent devices in flat panel displays, and in photovoltaic and sensor devices. Organic semiconductors may substantially reduce production costs as compared to inorganic materials such as silicon, as they can be deposited from solution, which can enable fast, large-area fabrication routes such as spin-coating, ink-jet printing, gravure printing, or transfer printing, to name a few.

The performance of an organic transistor can be evaluated by several parameters such as carrier mobility, current on/off ratio, threshold voltage, and/or on/off current magnitude. Materials such as pentacene, poly(thiophene), poly(thiophene-co-vinylene), poly(p-phenylene-co-vinylene) and oligo(3-hexylthiophene) have been studied for use in various electronic and optoelectronic applications. More recently, fused thiophene compounds have been found to have advantageous properties. For example, bisdithieno[3,2-b:2',3'-d] thiophene (1, j=2) has been found to efficiently π-stack in the solid state, possesses high mobility (up to 0.05 cm$^2$V·s), and has a high on/off ratio (up to 10$^8$). Oligomers and polymers of fused thiophenes, such as oligo- or poly(thieno[3,2-b] thiophene (2) and oligo- or poly(dithieno[3,2-b:2'-3'-d]thiophene) (1)

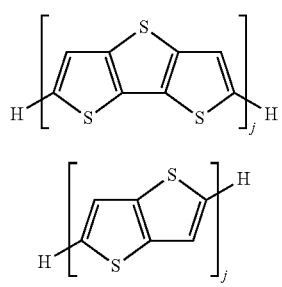

have also been suggested for use in electronic and optoelectronic devices, and have been shown to have acceptable conductivities and non-linear optical properties. However, unsubstituted fused thiophene-based materials tend to suffer from low solubility, marginal processability and oxidative instability. Thus, there remains a need for fused thiophene-based materials having improved solubility, processability and/or oxidative stability.

Applicant has described fused thiophene compounds and methods for making such compounds, for example, in U.S. Pat. Nos. 7,705,108; 7,714,098; 7,838,623; 7,893,191; 8,217,183; 8,278,346; 8,278,410; 8,349,998; 8,389,669; 8,487,114; 8,575,354; and 8,846,855, all of which are incorporated herein by reference in their entireties. However, methods for making such fused thiophene compounds have thus far suffered from various drawbacks, such as long reaction schemes, low yields, and/or high operating costs. Scale-up of existing processes for making fused thiophene compounds has been difficult to carry out in a cost-effective manner.

Accordingly, it would be advantageous to provide methods for producing fused thiophene compounds that utilize shorter reaction schemes, have improved yields, and/or are less complex and/or costly. Additionally, it would be advantageous to provide thiophene intermediate compounds that circumvent the need for multiple reaction steps for forming fused thiophene compounds. In various embodiments, fused thiophene compounds may be produced according to the methods herein using far fewer steps as compared to prior art methods and, thus, the disclosed methods may exhibit higher yields and/or faster production times. Methods for producing fused thiophene compounds disclosed herein may also be easier to scale up for commercial production.

SUMMARY

The disclosure relates, in various embodiments, to thiophene compounds of formulae (I), (I'), (II), (II'), (II''), and (II'''), and their use in methods for synthesizing fused thiophene compounds. Methods for making such compounds are also disclosed herein, as well as methods for making β-R-substituted fused thiophene compounds by coupling such compounds. β-R-substituted fused thiophene compounds made according to the disclosed methods and compounds or compositions comprising them may exhibit improved solubility, processability and/or oxidative stability. Furthermore, the synthesis methods disclosed herein may be shorter and/or less complex and/or costly than prior art methods for preparing β-R-substituted fused thiophene compounds.

Additional features and advantages of the disclosure will be set forth in the detailed description which follows, and in part will be readily apparent to those skilled in the art from that description or recognized by practicing the methods as described herein, including the detailed description which follows, the claims, as well as the appended drawings.

It is to be understood that both the foregoing general description and the following detailed description present various embodiments of the disclosure, and are intended to provide an overview or framework for understanding the nature and character of the claims. The accompanying drawings are included to provide a further understanding of the disclosure, and are incorporated into and constitute a part of this specification. The drawings illustrate various embodi-

BRIEF DESCRIPTION OF THE DRAWINGS

The following detailed description can be further understood when read in conjunction with the following drawings.

DETAILED DESCRIPTION

Compounds

Figure 1:
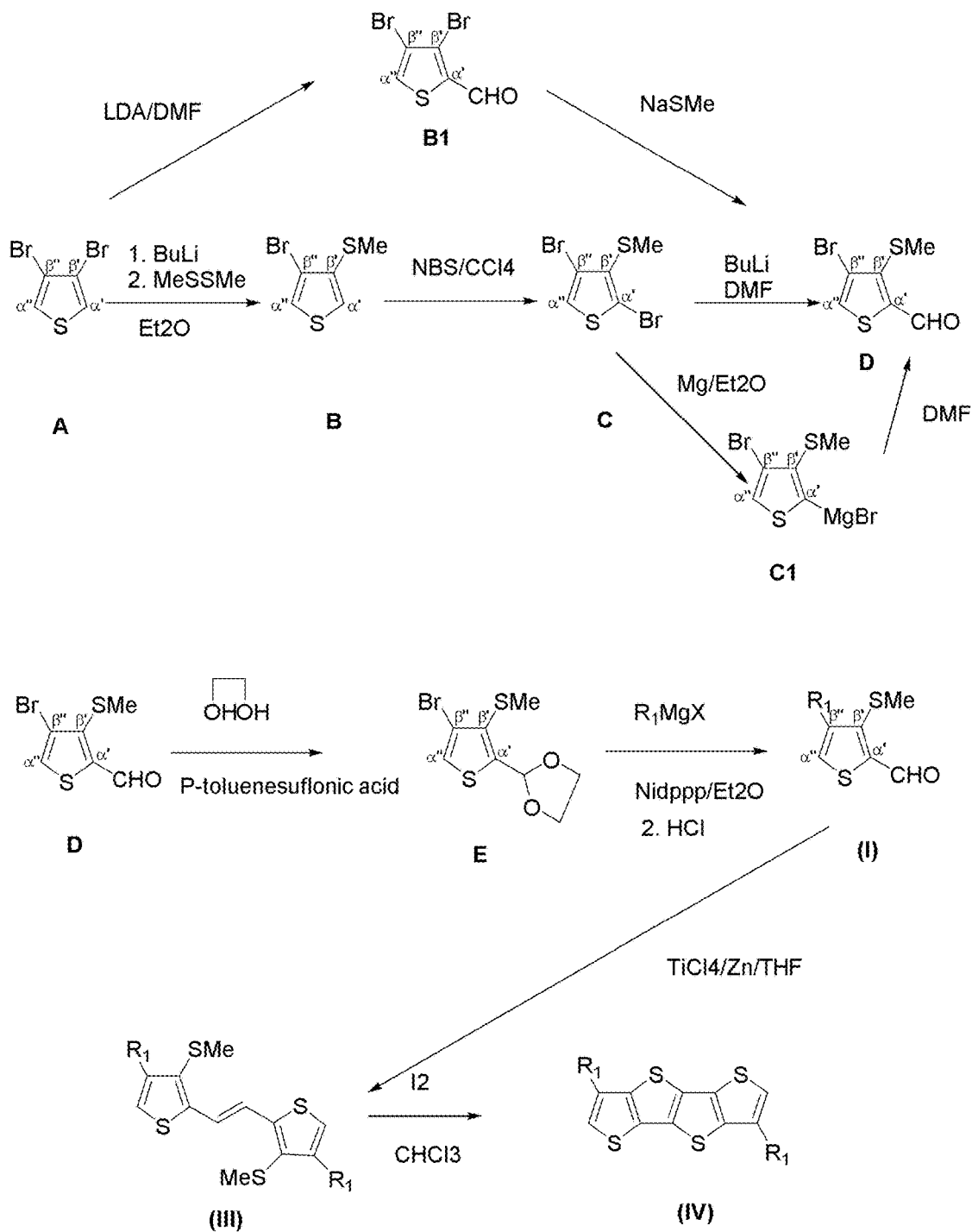
FIG. 1 is a reaction scheme for making a β-R-substituted fused thiophene compound comprising four fused rings (FT4) according to various embodiments of the disclosure.

Various aspects of the disclosure are described below with reference to specific embodiments, e.g., compounds and methods. However, it is to be understood that the disclosure and appended claims are not limited to specific compounds or synthetic methods, as such aspects may vary according to a particular application. It is also to be understood that the terminology used herein is for the purpose of describing various aspects only and is not intended to be limiting on the disclosure or the appended claims.

The term "alkyl" as used herein (e.g., alkyl group, etc.), is intended to denote a linear or branched saturated hydrocarbon. The alkyl can, for example, comprise from 1 to 48 carbon atoms, such as methyl, ethyl, n-propyl, isopropyl, n-butyl, isobutyl, t-butyl, pentyl, hexyl, heptyl, octyl, decyl, or tetradecyl, and the like. The term "unsubstituted alkyl" is intended to denote a group composed of carbon and hydrogen. The term "substituted alkyl" is intended to denote a group in which one or more of the hydrogen atoms is substituted with a different group, such as, for example, an aryl, cycloalkyl, aralkyl, alkenyl, alkynyl, ether, hydroxyl, alkoxy, thiol, thioalkyl, or halide group. Alkyl groups can also include "heteroalkyl" groups which can be interrupted by one or more heteroatoms, such as oxygen, nitrogen, sulfur, or phosphorous, e.g., at least one of the carbon atoms in the group can be substituted with a heteroatom.

The term "alkyl" can also include cycloalkyl groups. The term "cycloalkyl" as used herein is intended to denote a non-aromatic carbon-based ring composed of at least three carbon atoms. Examples of cycloalkyl groups include, but are not limited to, cyclopropyl, cyclobutyl, cyclopentyl, and cyclohexyl, to name a few. Cycloalkyl groups can also include heterocycloalkyl groups, where at least one of the carbon atoms of the ring is substituted with a heteroatom such as nitrogen, oxygen, sulfur, or phosphorus.

The term "aryl group" as used herein is intended to denote any carbon-based aromatic group including, but not limited to, benzene, naphthalene, and the like. Aryl groups can also include heteroaryl groups, where at least one heteroatom is incorporated within the ring of the aromatic group. Examples of heteroatoms include, but are not limited to, nitrogen, oxygen, sulfur, and phosphorus. The aryl group can be substituted or unsubstituted. The aryl group can, for instance, be substituted with one or more groups including, but not limited to, alkyl, alkynyl, alkenyl, aryl, halide, ether, hydroxy, or alkoxy groups.

The term "aralkyl" as used herein is intended to denote an aryl group having an alkyl group as defined above attached to the aryl group. An example of an aralkyl group is a benzyl group. The term "alkenyl" as used herein is intended to denote a linear or branched hydrocarbon group with a structural formula containing at least one carbon-carbon double bond. The term "alkynyl" as used herein is intended to denote a linear or branched hydrocarbon group with a structural formula containing at least one carbon-carbon triple bond. Alkenyl and alkynyl groups can comprise, for example, from 2 to 48 carbon atoms.

Disclosed herein are various compounds, compositions, and components for use in preparing fused thiophene compounds. These and other items may be disclosed herein as combinations, subsets, interactions, groups, and the like, such as specific compounds in a specific reaction scheme. However, it is to be understood that while specific reference to each various individual component or combinations of components may not be explicitly disclosed, such components or combinations thereof are contemplated as falling within the scope of the disclosure. Thus, if a class of molecules A, B, and C are disclosed as well as a class of molecules D, E, and F, along with an exemplary combination molecule A-D, even if each is not individually recited, each is individually and collectively contemplated. Thus, in this example, each of the combinations A-E, A-F, B-D, B-E, B-F, C-D, C-E, and C-F are contemplated and should be considered as part of the disclosure. Likewise, any subset or combination of these is also specifically contemplated and disclosed. This concept applies to all aspects of this disclosure including, but not limited to, method steps for making the disclosed compositions. Thus, if there are a variety of additional steps that can be performed it is understood that each of these additional steps can be performed with any specific embodiment or combination of embodiments of the disclosed methods, and that each such combination is specifically contemplated and should be considered as part of the disclosure.

Disclosed herein are thiophene compounds of formulae (I) and (I') which can, in some embodiments, be used to form β-R-substituted fused thiophene compounds:

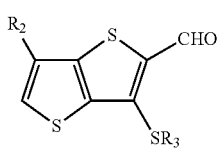

wherein $R_1$ and $R_2$ are independently chosen from alkyl, alkenyl, alkynyl, aryl, cycloalkyl, or aralkyl groups, which can be substituted or unsubstituted, linear or branched, and optionally interrupted by at least one heteroatom; and $R_3$ is chosen from $C_1$-$C_6$ linear alkyl radicals.

Also disclosed herein are compounds of formulae (II) and (II'), which can be used to form β-R-substituted fused thiophene compounds:

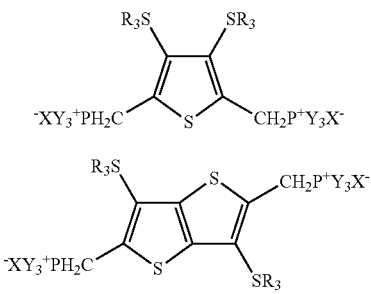

wherein $R_3$ is chosen from $C_1$-$C_6$ linear alkyl radicals; Y is chosen from butyl and phenyl groups; and $X^-$ is chosen from halogen ions, such as bromine, chlorine, and iodine ions.

Further disclosed herein are compounds of formulae (II") and (II'''), which can be used to form β-R-substituted fused thiophene compounds:

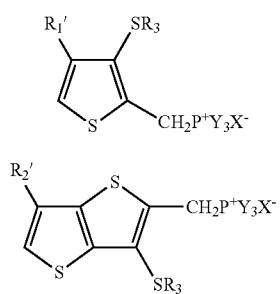

wherein $R_1'$ and $R_2'$ are independently chosen from alkyl, alkenyl, alkynyl, aryl, cycloalkyl, or aralkyl groups, which can be substituted or unsubstituted, linear or branched, and optionally interrupted by at least one heteroatom; $R_3$ is chosen from $C_1$-$C_6$ linear alkyl radicals; Y is chosen from butyl and phenyl groups; and $X^-$ is chosen from halogen ions, such as bromine, chlorine, and iodine ions.

According to various embodiments, in formulae (I), (I'), (II), (II'), (II"), and (II''') above $R_1$ and $R_2$ can be independently chosen from alkyl, alkenyl, alkynyl, aryl, cycloalkyl, or aralkyl groups, which can be substituted or unsubstituted, linear or branched, and optionally interrupted by at least one heteroatom. In certain embodiments, $R_1$ or $R_2$ can comprise from 1 to 48 carbon atoms, such as from 2 to 40 carbon atoms, from 3 to 36 carbon atoms, from 4 to 30 carbon atoms, from 6 to 24 carbon atoms, from 8 to 20 carbon atoms, or from 12 to 16 carbon atoms, including all ranges and subranges therebetween. According to various embodiments, $R_1$ and $R_2$ can be groups comprising at least 4 carbon atoms. For example, $R_1$ and $R_2$ can be chosen from $C_1$-$C_{36}$ linear alkyl groups or $C_3$-$C_{48}$ branched alkyl groups, which can be unsubstituted or substituted (substituted alkyl), and optionally interrupted by at least one heteroatom (heteroalkyl). In certain embodiments, $R_1$ and $R_2$ can be chosen from linear or branched alkyl groups comprising at least 4 carbon atoms.

When $R_1$ or $R_2$ is substituted, suitable substituents can be chosen, for example, from alkyl, alkenyl, alkynyl, aryl, cycloalkyl, aralkyl, ether, hydroxyl, alkoxy, thiol, thioalkyl, or halide, groups. When $R_1$ or $R_2$ is interrupted (hetero group), suitable heteroatoms can be chosen, for instance, from oxygen, nitrogen, sulfur, and phosphorous. When $R_1$ or $R_2$ is substituted, the substituents can similarly be substituted or interrupted with heteroatoms as described above. $R_3$ can be chosen, for example, from alkyl groups, such as $C_1$-$C_6$ linear alkyl groups (e.g., $C_2$, $C_3$, $C_4$, $C_5$, or $C_6$ linear alkyl radicals). According to various embodiments, the alkyl group $R_3$ is an ethyl or methyl group. In further embodiments, $R_3$ is a methyl group. According to still further embodiments, Y can be a butyl group and X' can be a bromine ion.

Compounds (I), (I'), (II), (II'), (II"), and (II''') can be used in the methods disclosed herein to form various fused thiophene compounds. The fused thiophene moieties described herein can have any number of fused rings. For example, the fused thiophene moieties can be tetracyclic (FT4), pentacyclic (FT5), hexacyclic (FT6), heptacyclic (FT7), octacyclic (FT8), nonacyclic (FT9), decacyclic (FT10), or higher, e.g., up to sixteen rings (FT16) or more. The methods disclosed herein can be used to form fused thiophene moieties that are substituted in the β-position by an R group. As used herein, an α position refers to a non-fused carbon center that is directly adjacent to the sulfur of the thiophene, while a β position refers to a non-fused carbon center that is separated from the sulfur by an α position. In formulae (IV), (IV'), (IV"), (IV'''), (VI), (VI'), (VIII), (VIII'), (VIII"), and (VIII''') below, which depict exemplary fused thiophene compounds, the α positions are unsubstituted, while the β positions are R-substituted.

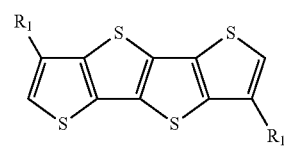

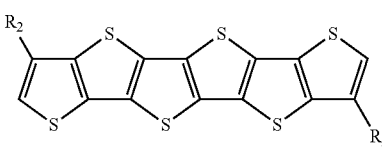

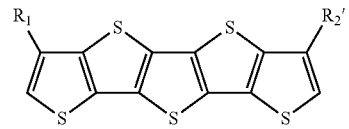

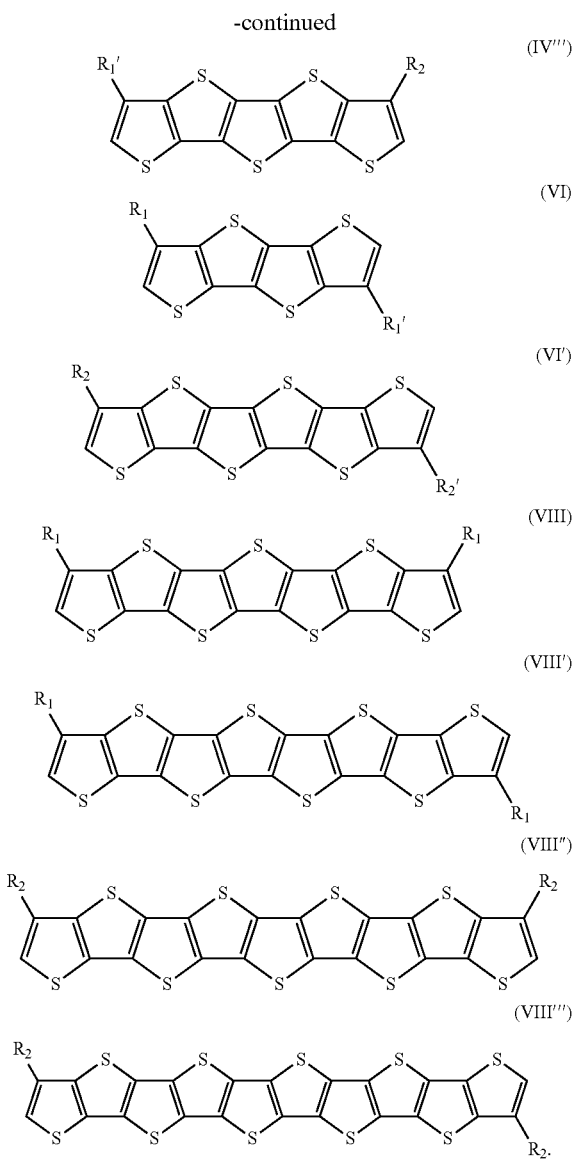

According to various aspects of the disclosure, $R_1$, $R_1'$, $R_2$, and $R_2'$ in the above formulae can be identical or different and can be independently chosen from any groups described with respect to the $R_1$, $R_1'$, $R_2$, and $R_2'$ substituents of compounds (I), (I'), (II"), and (II'") above. In certain embodiments, at least one of $R_1$, $R_1'$, $R_2$, or $R_2'$ can be an unsubstituted alkyl group. According to this aspect, the unsubstituted alkyl group can be a linear alkyl group (e.g., methyl, ethyl, propyl, butyl, pentyl, hexyl, heptyl, ocytl, nonyl, decyl, undecyl, dodecyl, hexadecyl, and so forth), a branched alky group (e.g., sec-butyl, neo-pentyl, 4-methylpentyl, etc.), or a substituted or unsubstituted cycloalkyl group (e.g., cyclopentyl, cyclohexyl, and the like). In other embodiments, at least one of $R_1$, $R_1'$, $R_2$, or $R_2'$ comprises at least four carbon atoms and is substituted or unsubstituted, and optionally interrupted with at least one heteroatom. For example, $R_1$, $R_1'$, $R_2$, and/or $R_2'$ can be substituted with at least one group chosen from alkyl, alkenyl, alkynyl, aryl, cycloalkyl, aralkyl, ether, hydroxyl, alkoxy, thiol, thioalkyl, or halide groups. Examples of substituted alkyl groups can include, for example, 6-hydroxyhexyl and 3-phenylbutyl, to name a few. The methods disclosed herein can be used to form β-R-substituted fused thiophene compounds having a wide variety of R groups, and the selection of these R groups (whether identical or different) can depend on the desired end use of the compound.

According to various embodiments, the fused thiophene compounds disclosed herein are substituted at both β positions. In other words, there are no β-hydrogens on the ring system. For example, in one aspect, neither R group ($R_1$, $R_1'$, $R_2$, or $R_2'$) in formulae (IV), (IV'), (IV") (IV'"), (VI), (VI'), (VIII), (VIII'), (VIII"), or (VIII'") are hydrogen. Such fused thiophenes may have increased oxidative stability and may be incorporated into more complex compounds having substantially no β-hydrogen content. For example, the fused thiophene compounds disclosed herein can exist as monomeric fused thiophenes or can be incorporated into more complex compounds, such as oligomers or polymers.

Alternatively, in other embodiments, any of the sulfur atoms of the β-R-substituted fused thiophene compounds can be oxidized to produce $SO_2$. The oxidized fused thiophene compounds can be prepared by oxidation, for example, with meta-chloroperoxybenzoic acid (MCPBA). Oxidation can be selective at the centralmost ring of the polycyclic structure; however, it is possible to oxidize any of the sulfur atoms in fused ring structure. The oxidized fused thiophene compounds can be incorporated into conjugated fused thiophene polymers or oligomers. The oxidized fused thiophene compounds can also be incorporated into a polymer comprising a polyester, a polyurethane, a polyamide, a polyketone, a polyacrylate, a polymethacrylate, or a poly(vinyl)ether to name a few.

In certain embodiments, the fused thiophene compounds prepared according to the methods disclosed herein can be incorporated into compositions for electronic or optoelectronic applications. For example, compositions comprising the fused thiophene compounds can comprise a total concentration of at least 1% by weight of fused thiophene, such as at least 2%, at least 3%, at least 5%, or at least 10% by weight of fused thiophene, including all ranges and subranges therebetween. According to various embodiments, the composition can have higher fused thiophene concentrations, such as up to about 20%, 30%, 40%, or 50% by weight of fused thiophene, including all ranges and subranges therebetween. Due to the R-substitution at the β positions, the fused thiophene compounds can have improved solubility in various solvents and can be used to produce compositions of relatively high concentration. Such compositions can be used to make a wide variety of devices, such as electronic, optoelectronic, or nonlinear optical devices. The compositions can be used, for example, in field effect transistors (FETs), thin film transistors (TFTs), organic light-emitting diodes (OLEDs), electro-optic (EO) applications, RFID tags, electroluminescent devices in flat panel displays, and photovoltaic and sensor devices, or as conductive materials, as two photon mixing materials, as organic semiconductors (OSs), or as non-linear optical (NLO) materials.

Methods

Described herein are methods for making fused thiophene compounds. In one embodiment, a method for making a β-R-substituted fused thiophene compound can comprise the steps of:

(i) coupling two compounds of formula (I) or two compounds of formula (I'):

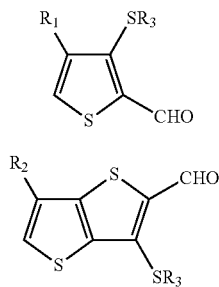

to form a compound of formula (III) or (III'):

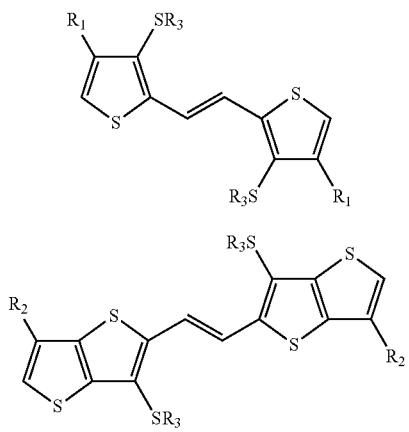

(ii) cyclizing the compound of formula (III) or (III') to form a compound of formula (IV) or (IV'):

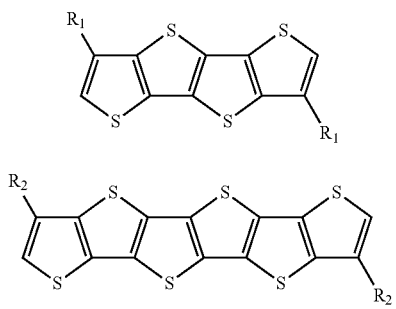

wherein $R_1$ are identical and are chosen from alkyl, heteroalkyl, alkenyl, alkynyl, aryl, heteroaryl, cycloalkyl, or aralkyl groups, which can be substituted or unsubstituted, linear or branched, and optionally interrupted by at least one heteroatom $R_3$ is chosen from linear $C_1$-$C_6$ alkyl radicals; and $R_2$ are identical and chosen from alkyl, heteroalkyl, alkenyl, alkynyl, aryl, heteroaryl, cycloalkyl, or aralkyl groups, which can be substituted or unsubstituted, linear or branched, and optionally interrupted by at least one heteroatom; and $R_3$ is chosen from $C_1$-$C_6$ linear alkyl radicals.

According to various embodiments, methods for forming compounds of formula (I) are also disclosed herein, the methods comprising the steps of:

(i) providing a β'-β''-halogen-substituted thiophene moiety of formula (A), wherein the halogen (X) is independently chosen from Br, Cl, and I;

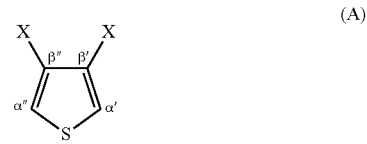

(ii) substituting a first β' or β'' halogen (X) with an alkylthio group —$SR_3$,
(iii) halogenating the thiophene moiety at an α' or α'' position adjacent the alkylthio group with a halogen (X') chosen from Br, Cl, and I;
(iv) substituting the α' or α'' halogen (X') with an aldehyde group (—C(O)H), and
(v) substituting a second β' or β''' halogen (X) with an alkyl group ($R_1$);
wherein $R_1$ and $R_3$ are defined as above.

In further embodiments, methods for forming compounds of formula
(I') are disclosed herein, the methods comprising the steps of:
(i) providing a β'-β''-halogen-substituted thiophene moiety of formula (A'), wherein the halogen (X) is independently chosen from Br, Cl, and I;

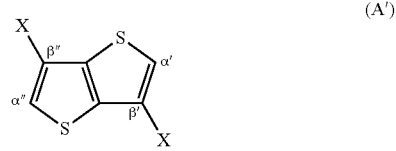

(ii) substituting a first β' or β'' halogen (X) with an alkylthio group (—$SR_3$),
(iii) halogenating the thiophene moiety at an α' or α'' position adjacent the alkylthio group with a halogen (X') chosen from Br, Cl, and I;
(iv) substituting the α' or α'' halogen (X') with an aldehyde group (—C(O)H); and
(v) substituting a second β' or β'' halogen (X) with an alkyl group ($R_2$);
wherein $R_2$ and $R_3$ are defined as above.

Figure 2:
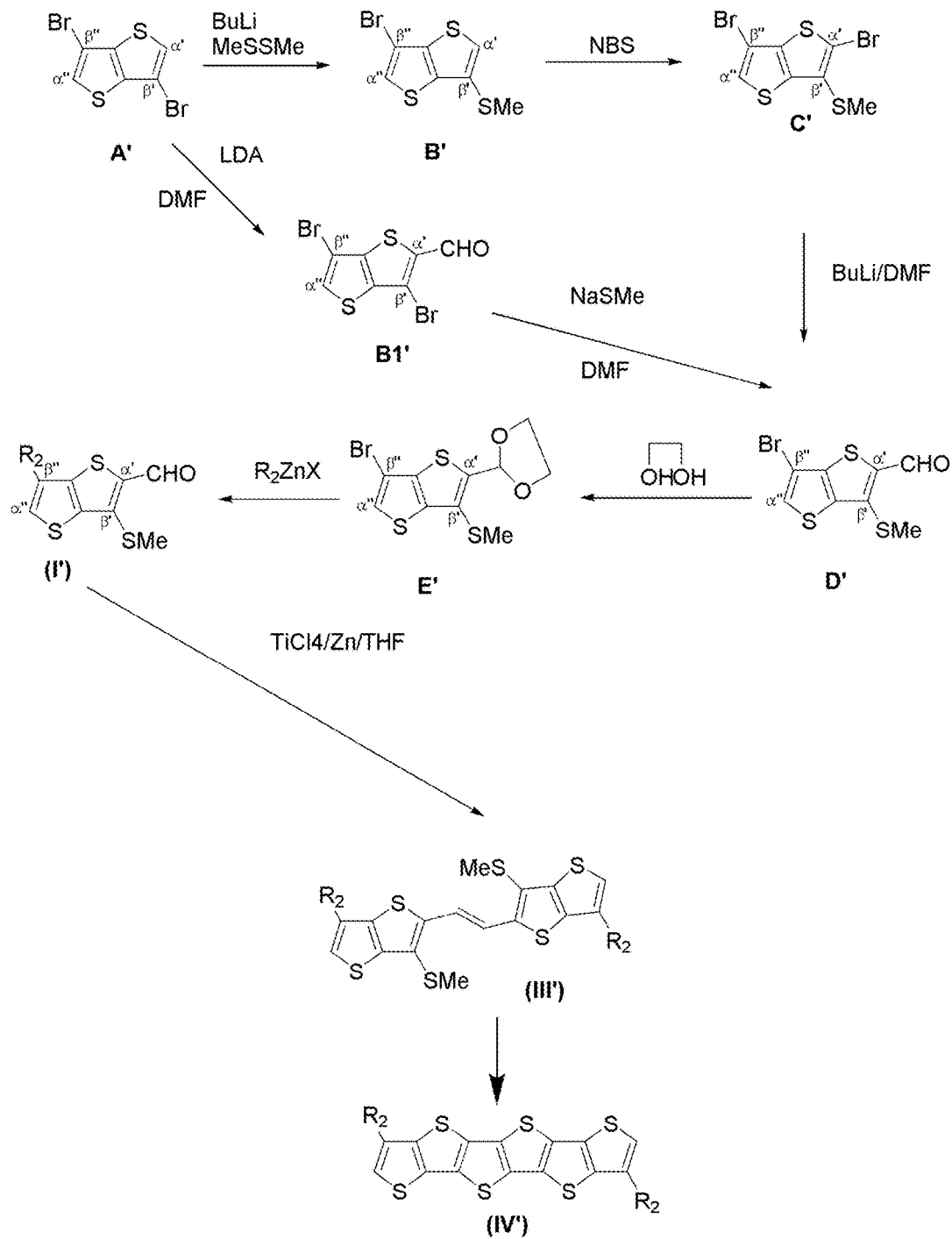
FIG. 2 is a reaction scheme for making a β-R-substituted fused thiophene compound comprising six fused rings (FT6) according to various embodiments of the disclosure.
Figure 3:
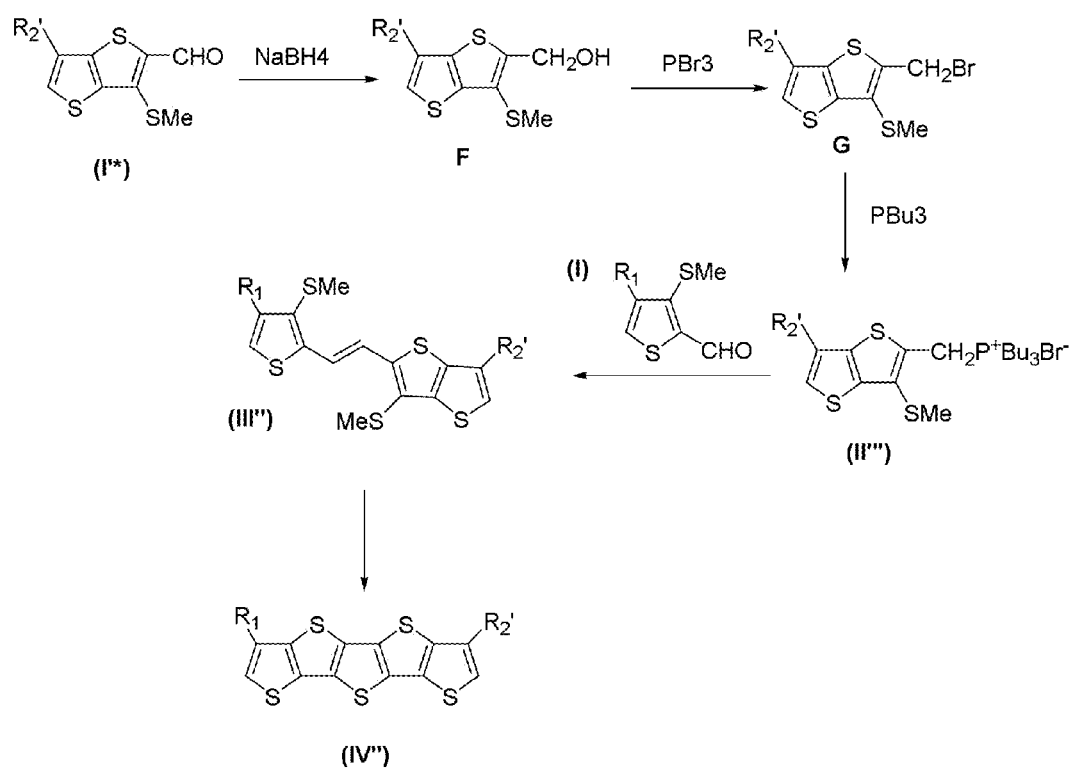
FIG. 3 is a reaction scheme for making a β-R-substituted fused thiophene compound comprising five fused rings (FT5) according to various embodiments of the disclosure.

FIG. 1 depicts an exemplary reaction scheme for making a β-R-substituted fused thiophene compound. The reaction scheme depicted in FIG. 1 comprises the steps of forming a thiophene compound of formula (I) and coupling two compounds of formula (I) to form a β-R-substituted fused thiophene compound comprising four fused rings (FT4). Similarly, FIG. 2 depicts an exemplary reaction scheme for making a β-R-substituted fused thiophene compound. In FIG. 2 a thiophene compound of formula (I') is formed and two such compounds are coupled to form a β-R-substituted fused thiophene compound comprising six fused rings (FT6). FIG. 3 illustrates an exemplary embodiment in which a compound of formula (I) and a compound of formula (I') can be coupled to form a β-R-substituted fused thiophene compound comprising five fused rings (FT5).

Of course, it is to be understood that the reaction schemes depicted in FIGS. 1-3 include specific substituents and reagents solely for the purposes of illustration and such components are not intended to be limiting on the disclosure or appended claims. Moreover, while FIGS. 1-2 illustrate complete reaction schemes comprising steps for making compounds of formulae (I) and (I') and subsequently coupling such compounds, it is to be understood that the appended claims are not so limited and may include one or more portions of the illustrated reaction schemes. Similarly, while FIG. 3 illustrates a partial reaction scheme comprising steps for coupling compounds of formulae (I) and (I'), it is to be understood that the appended claims are not so limited and may further include steps for making compounds of formulae (I) and (I').

Referring in more detail to FIG. 1, a β',β"-halogen-substituted compound of formula (A) (X=Br illustrated) is provided:

(A)

Compound (A) can then be substituted with an alkylthio group (—SCH$_3$ illustrated) at the β' or β" position (β' illustrated). Such a substitution can be carried out, e.g., using butyl lithium (BuLi) and dimethylsulfide (MeSSMe) in the presence of diethyl ether (Et$_2$O) according to a reaction described in Baurle et al. "Synthesis and Properties of a Series of Methyltio Oligothiophenes," Liebigs Ann., pp. 279-284 (1996).

Compound (B) can then be halogenated at the α' or α" position adjacent the alkylthio group (α' illustrated) with a halogen (X') (X'=Br illustrated). For example, a selective halogenation reaction can be carried out, e.g., selective bromination using n-bromosuccinimide (NBS) and carbon tetrachloride (CCl$_4$). The α' (or α") halogen of compound (C) can then be substituted with an aldehyde group (—C(O)H) using any suitable reaction. For instance, a formylation reaction can be carried out using BuLi and dimethylformamide (DMF) to give compound (D). Alternatively, compound (C) can be reacted with magnesium (Mg) in the presence of Et$_2$O to form a Grignard reagent (C1), which can then be reacted with DMF in a Grignard reaction to give compound (D). The α" (or α') halogen (X=Br illustrated) of compound (D) can then be replaced with alkyl group R$_1$ using any suitable reaction. In various embodiments, the α' (or α") aldehyde function can be protected by reaction with ethylene glycol and p-toluenesulfonic acid to produce compound (E). Compound (E) can then be reacted with a Grignard reagent (R$_1$MgX illustrated) in the presence of a catalyst (NidpppCl$_2$ illustrated) and Et$_2$O to exchange the halogen for an R$_1$ group via metathesis reaction to give the compound of formula (I).

Alternatively, Compound (A) can be converted to Compound (D) via a two-step reaction through Compound (B1). The first reaction step comprises reacting lithium diisopropylamide (or an alternative strong base) in DMF with Compound (A) to form the α' (or α") aldehyde substituted compound, Compound (B1). The second step involves reacting Compound (B1) with a sodium alkylsulfide (shown as NaSMe) to produce Compound (D).

Two compounds of formula (I) can then be coupled together using any suitable reaction. As illustrated, a McMurry coupling can be carried out using titanium tetrachloride (TiCl$_4$), zinc (Zn), and tetrahydrofuran (THF) to yield a compound of formula (III). During coupling, the aldehyde functions of the compounds react to form a C=C double bond between the two compounds. Alternatively, a Wittig coupling reaction can also be used, as described in more detail with respect to FIG. 3. Compound (III) can then be cyclized to yield the β-R-substituted fused thiophene compound of formula (IV) comprising four fused rings (FT4). Cyclization can be carried out, for example, via an iodine (I2)-mediated cyclization reaction in the presence of chloroform (CHCl$_3$). In various embodiments, McMurry coupling according to the scheme illustrated in FIG. 1 can be used to create symmetrical fused thiophene compounds (e.g., compounds with identical R$_1$ groups).

Referring in more detail to FIG. 2, a β',β"-halogen-substituted compound of formula (A') (X=Br illustrated) is provided:

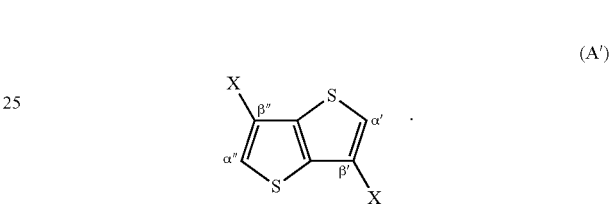

(A')

Compound (A') can then be substituted with an alkylthio group (—SCH$_3$ illustrated) at the β' or β" position (β' illustrated). Such a substitution can be carried out, e.g., using butyl lithium (BuLi) and dimethylsulfide (MeSSMe) according to a reaction described in Baurle et al.

Compound (B') can then be halogenated at the α' or α" position adjacent the alkylthio group (α' illustrated) with a halogen (X') (X'=Br illustrated). For example, a selective halogenation reaction can be carried out, e.g., selective bromination using n-bromosuccinimide (NBS) and carbon tetrachloride (CCl$_4$). The α' (or α") halogen of compound (C') can then be substituted with an aldehyde group (—C(O)H) using any suitable reaction. For instance, a formylation reaction can be carried out using BuLi and dimethylformamide (DMF) to give compound (D'). The α" (or α') halogen (X=Br illustrated) of compound (D') can then be replaced with alkyl group R$_2$ using any suitable reaction. In various embodiments, the α' (or α") aldehyde function can be protected by reaction with ethylene glycol and p-toluenesulfonic acid to produce compound (E'). Compound (E') can then be reacted with a Grignard reagent (R$_2$ZnX illustrated) to exchange the halogen for an R$_2$ group via a metathesis reaction to give the compound of formula (I').

Alternatively, Compound (A') can be converted to Compound (D') via a two-step reaction through Compound (B1'). The first reaction step comprises reacting lithium diisopropylamide (or an alternative strong base) in DMF with Compound (A') to form the α' (or α") aldehyde substituted compound, Compound (B1'). The second step involves reacting Compound (B1') with a sodium alkylsulfide (shown as NaSMe) to produce Compound (D').

Two compounds of formula (I') can then be coupled together using any suitable reaction. As illustrated, a McMurry coupling can be carried out using titanium tetrachloride (TiCl$_4$), zinc (Zn), and tetrahydrofuran (THF) to yield a compound of formula (III'). During coupling, the aldehyde functions of the compounds react to form a C=C double bond between the two compounds. Alternatively, a Wittig coupling reaction can be used to couple the compounds of formula (I'), as described in more detail with respect to FIG. 3. Compound (III') can then be cyclized to yield the β-R-substituted fused thiophene compound of formula (IV') comprising six fused rings (FT6). Cyclization can be carried out, for example, via an iodine (I2)-mediated cyclization reaction in the presence of chloroform (CHCl₃). In various embodiments, McMurry coupling according to the scheme illustrated in FIG. 2 can be used to create symmetrical fused thiophene compounds (e.g., compounds with identical R₂ groups).

Referring to FIG. 3, compounds (I) and (I') can also be modified and coupled together via a Wittig coupling reaction. For example, the aldehyde function of compound (I') can be replaced with a phosphine function (—CH₂P⁺Bu₃Br⁻ illustrated) and the compound thus modified can react with compound (I) to produce a compound of formula (III'''). For example, the aldehyde function of compound (I*) (R₂=R₂') can be reduced to an alcohol function (—CH₂OH) using sodium borohydride (NaBH₄), and the hydroxyl group (—OH) of compound (F) can then be substituted with a halogen (X'') (X''=Br illustrated) via reaction with a phosphorous trihalide (PX''₃) (X''=Br illustrated). Reaction of compound (G) with tributylphosphine (PBu₃) (illustrated) or triphenyl phosphine (PPh₃) can then yield a phosphine-modified compound (II'''), which can react with compound (I) to yield the compound of formula (III''). Compound (III'') can then be cyclized to yield the β-R-substituted fused thiophene compound of formula (IV'') comprising five fused rings (FT5), in which R₁ and R₂' can be identical or different. In various embodiments, Wittig coupling according to the scheme illustrated in FIG. 3 can be used to create symmetrical or asymmetrical fused thiophene compounds (e.g., compounds with identical or different R₁ and R₂' groups).

Figure 4:
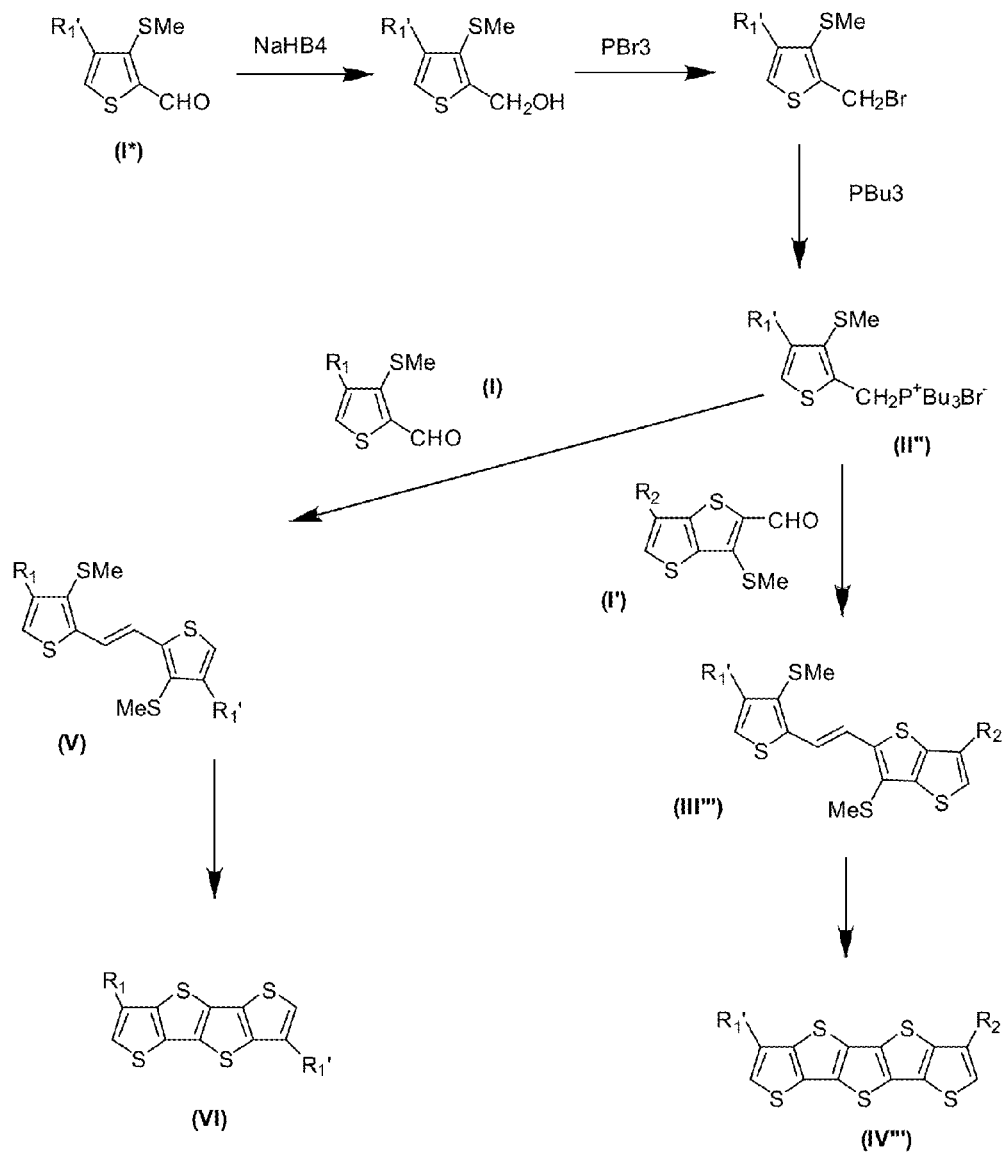
FIG. 4 is a reaction scheme for making β-R-substituted fused thiophene compounds comprising four or five fused rings (FT4, FT5) according to various embodiments of the disclosure.

Alternatively, as illustrated in FIG. 4 (right-hand side), compound (I*) (R₁=R₁') can be modified with a phosphine function to produce compound (II''), which can be reacted with compound (I') to produce a compound of formula (III'''), which can be cyclized to give the compound of formula (IV'''), in which R₁' and R₂ can be identical or different. In other embodiments, as illustrated in FIG. 4 (left-hand side), the Wittig coupling reaction can be used to form compounds of formula (V) (illustrated) and (V') (not illustrated) by reacting a phosphine-modified compound (II'') with an unmodified compound (I) (illustrated), or a phosphine-modified compound (II''') with an unmodified compound (I') (not illustrated), respectively. Compound (V) can be cyclized to form compounds of formula (VI) in which R₁ and R₁' are identical or different. Similarly, compound (V') (not illustrated) can be cyclized to form compounds of formula (VI') (not illustrated), in which R₂ and R₂' are identical or different. In various embodiments, Wittig coupling according to the scheme illustrated in FIG. 4 can be used to create symmetrical or asymmetrical fused thiophene compounds (e.g., compounds with identical or different R₁ and R₁' groups or compounds with identical or different R₁' and R₂ groups).

Thus, while R₁, R₁', R₂, and R₂' can be chosen from the same groups according to some embodiments (alkyl, alkenyl, alkynyl, aryl, cycloalkyl, or aralkyl groups, which can be substituted or unsubstituted, linear or branched, and optionally interrupted by at least one heteroatom), each of these substituents can be "independently" chosen from this list, which is intended to denote that each radical R₁ can be different from any other R₁', R₂, or R₂' radical in the same compound, and vice versa. In other embodiments, fused thiophene compounds disclosed herein can comprise identical R substituents, such as identical R₁, R₁', R₂, R₂' or even R₃ substituents.

According to various embodiments, methods for making β-R-substituted fused thiophene compounds are disclosed herein, the methods comprising:

(i) coupling a first compound chosen from compounds of formulae (I) and (I'):

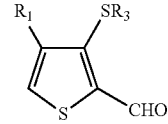

(I)

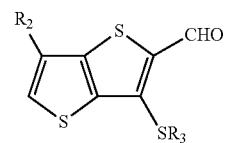

(I')

with a second compound chosen from compounds of formula (II'') or (II'''):

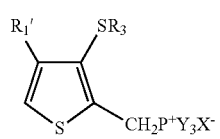

(II'')

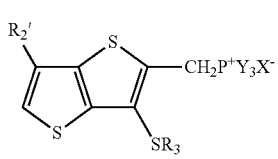

(II''')

to form a third compound of formula (III''), (III'''), (V) or (V'):

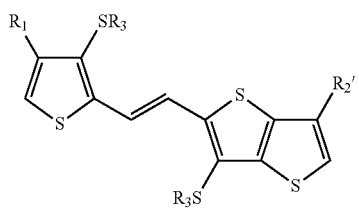

(III'')

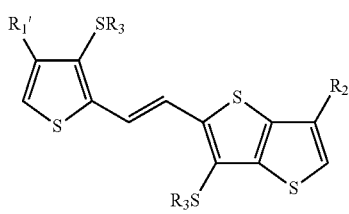

(III''')

-continued

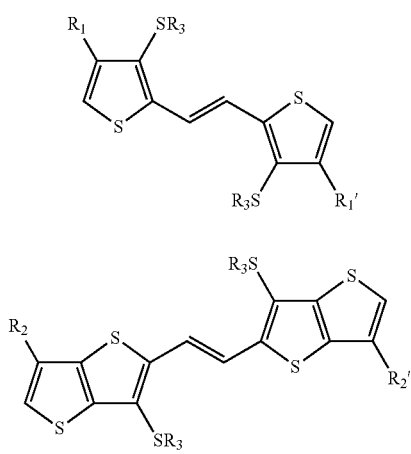

(V)

(V')

(ii) cyclizing the compound of formula (III''', (III''''), (V), or (V') to form a compound of formula (IV''), (IV''''), (VI), or (VI'):

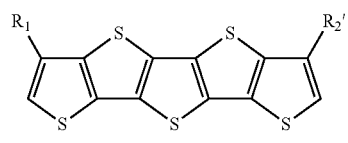

(IV'')

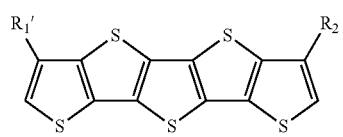

(IV'''')

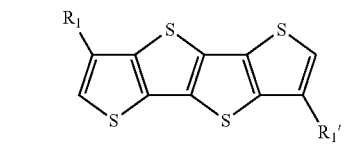

(VI)

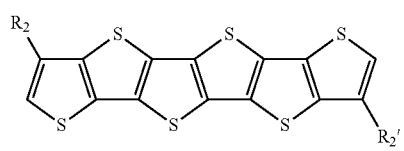

(VI')

wherein $R_1$, $R_1'$, $R_2$, and $R_2'$, which are identical or different, are independently chosen from alkyl, alkenyl, alkynyl, aryl, cycloalkyl, or aralkyl groups, which can be substituted or unsubstituted, linear or branched, and optionally interrupted by at least one heteroatom; $R_3$ is chosen from linear $C_1$-$C_6$ alkyl radicals; Y is chosen from butyl and phenyl groups; and $X^-$ is chosen from halogen ions.

Methods for making thiophene compounds of formula (II'') are also disclosed herein, the methods comprising:

(i) providing a compound of formula (I*):

(I*)

(ii) reducing the aldehyde group (—C(O)H) to an alcohol group (—CH$_2$OH), (iii) substituting the hydroxyl group (—OH) of the alcohol group with a halogen (X) chosen from Br, Cl, and I; and (iv) reacting the compound formed in step (vi) with tributylphosphine (PBu$_3$) or triphenyl phosphine (PPh$_3$).

Further disclosed herein are methods for making compounds of formula (II'''), the methods comprising:

providing a compound of formula (I'*):

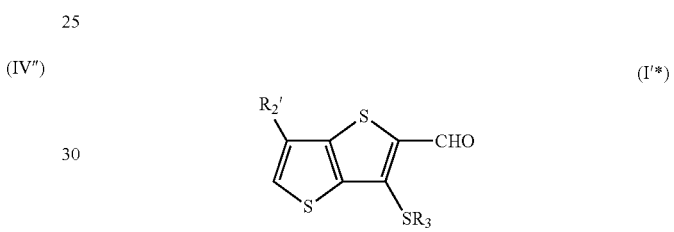

(I'*)

(ii) reducing the aldehyde group (—C(O)H) to an alcohol group (—CH$_2$OH);

(iii) substituting the hydroxyl group (—OH) of the alcohol group with a halogen (X) chosen from Br, Cl, and I; and (iv) reacting the compound formed in step (vi) with tributylphosphine (PBu$_3$) or triphenyl phosphine (PPh$_3$).

According to additional embodiments, compounds (I) and (I') can also be coupled with compounds of formulae (II) and (II') to produce β-R-substituted fused thiophene compounds. Such methods can comprise, for example, the steps of:

(i) coupling a first compound chosen from compounds of formulae (I) and (I'):

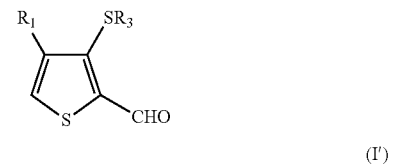

(I)

(I')

with a second compound chosen from compounds of formulae (II) or (II'):

(II)
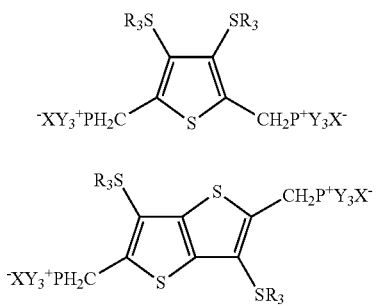

(II')
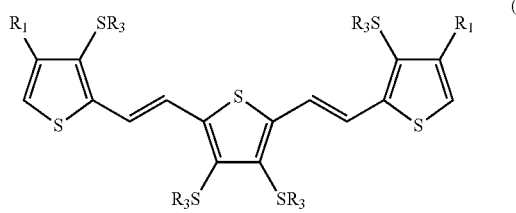

to form a third compound of formula (VII), (VII'), (VII''), or (VII'''):

(VII)
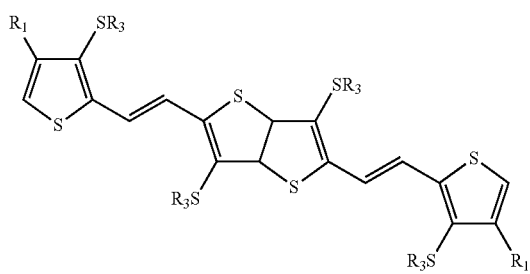

(VII')
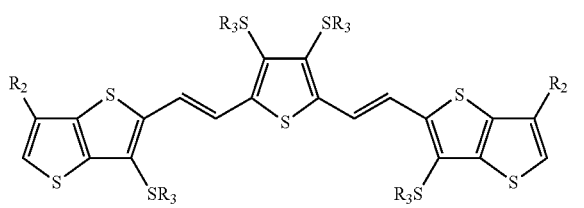

(VII'')
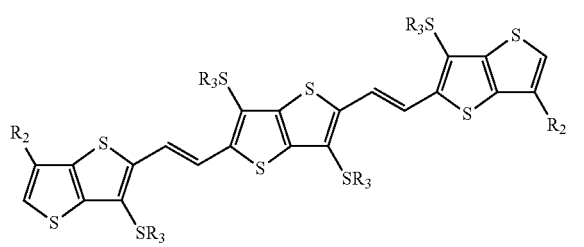

(VII''')

(ii) cyclizing the compound of formula (VII), (VII'), (VII''), or (VII''') to form a compound of formula (VIII), (VIII'), (VIII''), or (VIII'''):

(VIII)

(VIII')
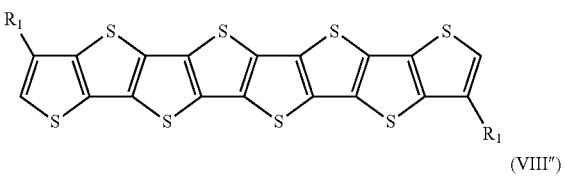

(VIII'')
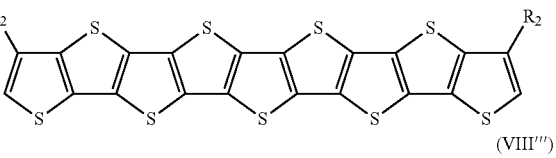

(VIII''')
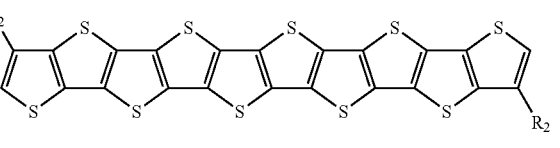

wherein $R_1$ are identical and are independently chosen from alkyl, alkenyl, alkynyl, aryl, cycloalkyl, or aralkyl groups, which can be substituted or unsubstituted, linear or branched, and optionally interrupted by at least one heteroatom; $R_2$ are identical and are independently chosen from alkyl, alkenyl, alkynyl, aryl, cycloalkyl, or aralkyl groups, which can be substituted or unsubstituted, linear or branched, and optionally interrupted by at least one heteroatom; $R_3$ is chosen from linear $C_1$-$C_6$ alkyl radicals; Y is chosen from butyl and phenyl groups; and $X^-$ is chosen from halogen ions.

Figure 5:
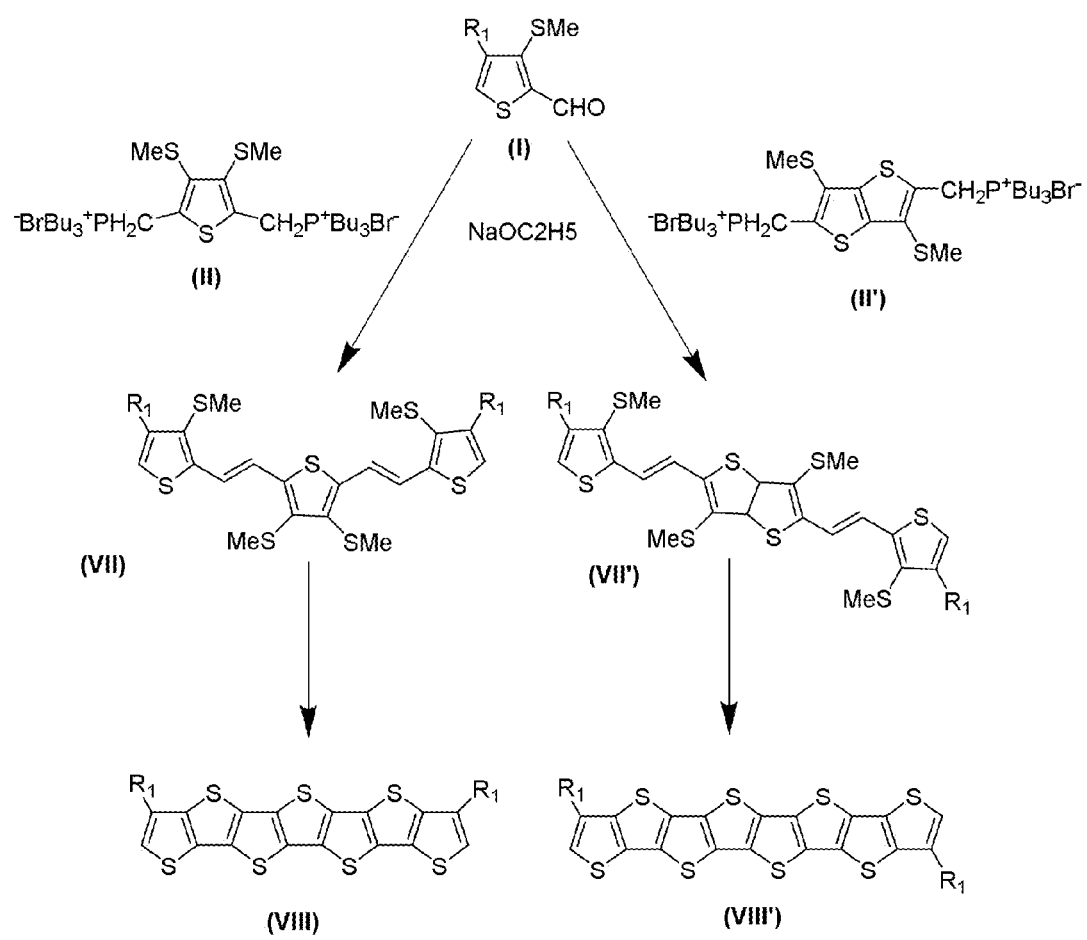
FIG. 5 is a reaction scheme for making a β-R-substituted fused thiophene compound comprising seven or eight fused rings (FT7, FT8) according to various embodiments of the disclosure.
Figure 6:
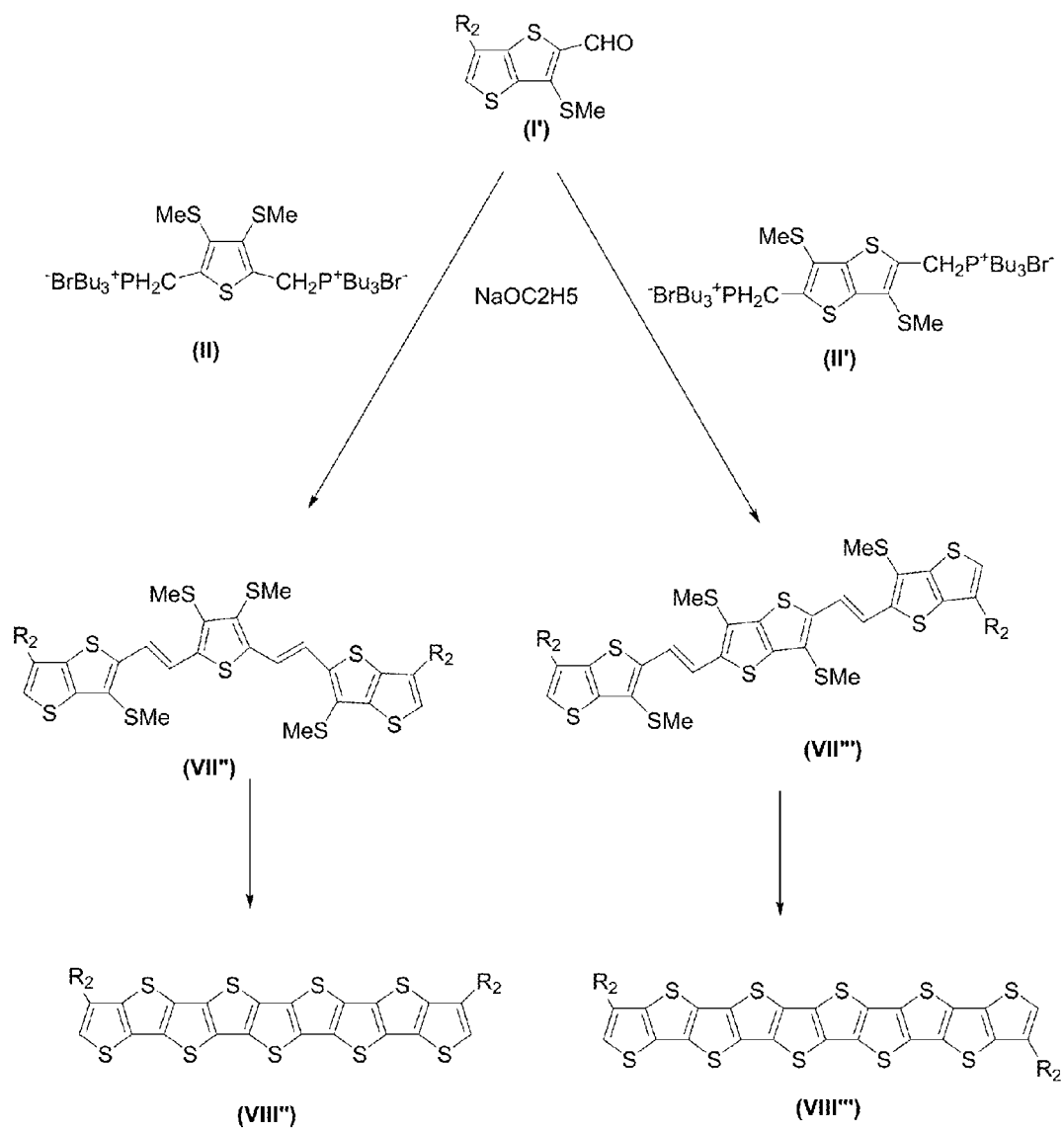
FIG. 6 is a reaction scheme for making a β-R-substituted fused thiophene compound comprising nine or ten fused rings (FT9, FT10) according to various embodiments of the disclosure.

An exemplary reaction scheme for coupling compounds of formula (I) with compounds of formulae (II) or (II') is illustrated in FIG. 5. Compound (I) can be coupled, e.g., via a Wittig coupling reaction, with compound (II) or (II') (X=Br, Y=Bu illustrated) to form compounds (VII) and (VII'). These compounds can then be cyclized to form β-R-substituted fused thiophene compounds of formulae (VIII) and (VIII'), having seven (FT7) or eight (FT8) fused rings, respectively. Similarly, FIG. 6 depicts an exemplary reaction scheme for coupling compounds of formula (I') with compounds of formulae (II) or (II'). Compound (I') can be coupled, e.g., via a Wittig coupling reaction, with compound (II) or (II') (X=Br, Y=Bu illustrated) to form compounds (VII'') and (VII'''). These compounds can then be cyclized to form β-R-substituted fused thiophene compounds of formulae (VIII'') and (VIII'''), having nine (FT9) or ten (FT10) fused rings, respectively. In non-limiting embodiments, Wittig coupling according to the scheme illustrated in FIGS. 5-6 can be used to create symmetrical fused thiophene compounds (e.g., compounds with identical $R_1$ or compounds with identical $R_2$ groups).

According to various embodiments, methods for forming compounds of formula (II) are also disclosed herein, the methods comprising the steps of:

(i) providing a β'-β"-halogen-substituted thiophene moiety of formula (A), wherein the halogen (X) is independently chosen from Br, Cl, and I;

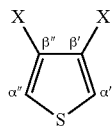

(A)

(ii) substituting the β' and β" halogens (X) with alkylthio groups (—SR₃),
(iii) halogenating the thiophene moiety at the α' and α" positions with a halogen (X') independently chosen from Br, Cl, and I;
(iv) substituting the α' and α" halogens (X') with aldehyde groups (—C(O)H);
(v) reducing the α' and α" aldehyde groups (—C(O)H) to alcohol groups (—CH₂OH),
(vi) substituting the hydroxyl (—OH) of the α' and α" alcohol groups with a halogen (X") chosen from Br, Cl, and I; and
(vii) reacting the compound formed in step (vi) with tributylphosphine (PBu₃) or triphenyl phosphine (PPh₃).

Figure 7A:
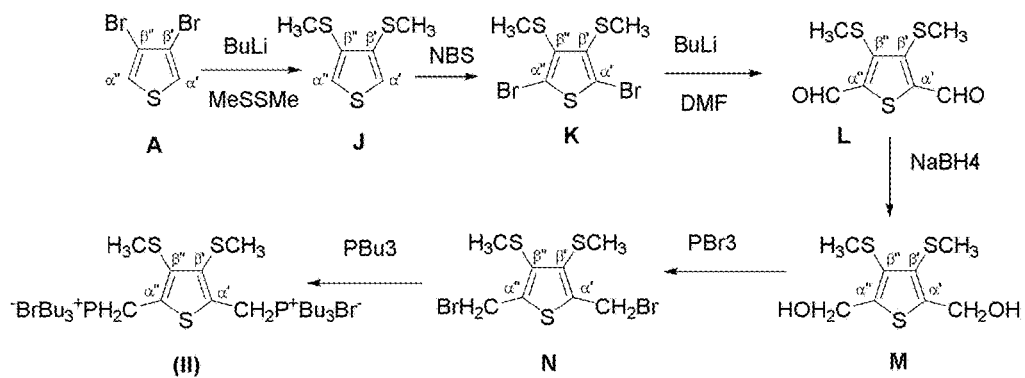
FIGS. 7A-B are reaction schemes for making thiophene compounds of formulae (II) and (II') according to various embodiments of the disclosure.

FIG. 7A depicts an exemplary reaction scheme for making a compound of formula (II). In the illustrated reaction, a β',β"-halogen-substituted compound of formula (A) (X=Br illustrated) is provided. Compound (A) can then be substituted with an alkylthio group (—SCH₃ illustrated) at the β' and β" positions. Such a substitution can be carried out, e.g., using butyl lithium (BuLi) and dimethylsulfide (MeSSMe) in the presence of diethyl ether (Et₂O) according to a reaction described in Baurle et al. Compound (J) can then be halogenated at the α' and α" positions with a halogen (X') (X'=Br illustrated). For example, a halogenation reaction can be carried out, e.g., bromination using n-bromo-succinimide (NBS) and carbon tetrachloride (CCl₄). The α' and α" halogens of compound (K) can then be substituted with an aldehyde group (—C(O)H) using any suitable reaction. For instance, a formylation reaction can be carried out using BuLi and dimethylformamide (DMF) to give compound (L). The α' and α" aldehyde groups can then be reduced to alcohol (methanol) groups using any suitable reaction. In various embodiments, the α' and α" aldehyde groups can be reduced using sodium borohydride (NaBH₄), and the hydroxyl group (—OH) of compound (M) can then be substituted with a halogen (X") (X"=Br illustrated) via reaction with a phosphorous trihalide (PX"₃) (X"=Br illustrated). Reaction of compound (N) with tributylphosphine (PBu₃) (illustrated) or triphenyl phosphine (PPh₃) can then yield the compound of formula (II).

In further embodiments, methods for forming compounds of formula (II') are also disclosed herein, the methods comprising the steps of:
(i) providing a β'-β"-halogen-substituted thiophene moiety of formula (A'), wherein the halogen (X) is independently chosen from Br, Cl, and I;

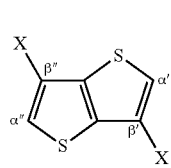

(A')

(ii) substituting the β' and β" halogens (X) with alkylthio groups (—SR₃),
(iii) halogenating the thiophene moiety at the α' and α" positions with a halogen (X') independently chosen from Br, Cl, and I;
(iv) substituting the α' and α" halogens (X') with aldehyde groups (—C(O)H);
(v) reducing the α' and α" aldehyde groups (—C(O)H) to alcohol groups (—CH₂OH),
(vi) substituting the hydroxyl (—OH) of the α' and α" alcohol groups with a halogen (X") chosen from Br, Cl, and I; and
(vii) reacting the compound formed in step (vi) with tributylphosphine (PBu₃) or triphenyl phosphine (PPh₃).

Figure 7B:
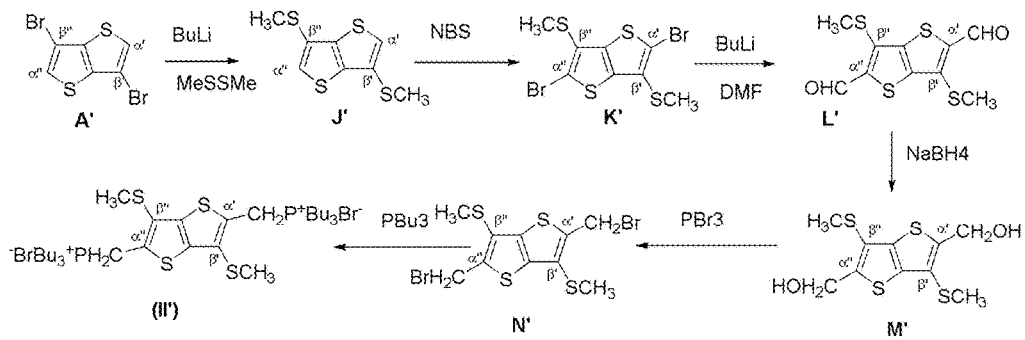

FIG. 7B depicts an exemplary reaction scheme for making a compound of formula (II'). In the illustrated reaction, a β',β"-halogen-substituted compound of formula (A') (X=Br illustrated) is provided. Compound (A') can then be substituted with an alkylthio group (—SCH₃ illustrated) at the β' and β" positions. Such a substitution can be carried out, e.g., using butyl lithium (BuLi) and dimethylsulfide (MeSSMe) in the presence of diethyl ether (Et₂O) according to a reaction described in Baurle et al. Compound (J') can then be halogenated at the α' and a" positions with a halogen (X') (X'=Br illustrated). For example, a halogenation reaction can be carried out, e.g., bromination using n-bromo-succinimide (NBS) and carbon tetrachloride (CCl₄). The α' and α" halogens of compound (K') can then be substituted with an aldehyde group (—C(O)H) using any suitable reaction. For instance, a formylation reaction can be carried out using BuLi and dimethylformamide (DMF) to give compound (L'). The α' and α" aldehyde groups can then be reduced to alcohol (methanol) groups using any suitable reaction. In various embodiments, the α' and α" aldehyde groups can be reduced using sodium borohydride (NaBH₄), and the hydroxyl group (—OH) of compound (M') can then be substituted with a halogen (X") (X"=Br illustrated) via reaction with a phosphorous trihalide (PX"₃) (X"=Br illustrated). Reaction of compound (N') with tributylphosphine (PBu₃) (illustrated) or triphenyl phosphine (PPh₃) can then yield the compound of formula (II').

It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "a compound" includes examples having two or more such compounds unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C.

It will be apparent to those skilled in the art that various modifications and variations can be made to the present disclosure without departing from the spirit and scope of the disclosure. Since modifications combinations, sub-combinations and variations of the disclosed embodiments incorporating the spirit and substance of the disclosure may occur to persons skilled in the art, the disclosure should be construed to include everything within the scope of the appended claims and their equivalents.

What is claimed is:

1. A thiophene compound of formula (I), (I'), (II), (II'), (II"), or (II'''):

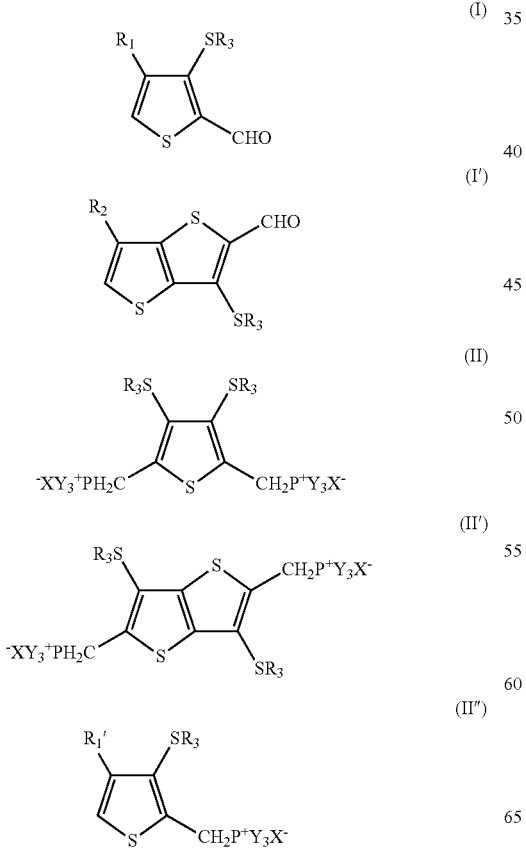

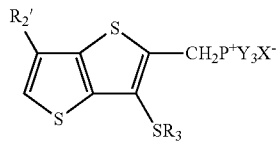

wherein $R_1$, $R_1'$, $R_2$, and $R_2'$ comprise at least four carbon atoms and are independently chosen from alkyl, alkenyl, alkynyl, aryl, cycloalkyl, or aralkyl groups, which can be substituted or unsubstituted, linear or branched, and optionally interrupted by at least one heteroatom; $R_3$ is chosen from $C_1$-$C_6$ linear alkyl radicals;

Y is chosen from butyl and phenyl groups; and $X^-$ is chosen from halogen ions.

2. The thiophene compound of formula (I), (I'), (II"), or (II''') according to claim 1, wherein $R_1$, $R_2$, $R_1'$, and $R_2'$ are independently chosen from $C_1$-$C_{36}$ linear alkyl groups and $C_3$-$C_{48}$ branched alkyl groups.

3. The thiophene compound of formula (I), (I'), (II"), or (II''') according to claim 1, wherein $R_1$, $R_2$, $R_1'$, and $R_2'$ are substituted with at least one group chosen from alkyl, alkenyl, alkynyl, aryl, cycloalkyl, aralkyl, ether, hydroxyl, alkoxy, thiol, thioalkyl, and halide groups.

4. The thiophene compound of formula (II), (II'), (II"), or (II''') according to claim 1, wherein Y is a butyl group and $X^-$ is a bromine ion.

5. A method for making the thiophene compound of formula (I) according to claim 1, comprising:
(i) providing a β'-β"-halogen-substituted thiophene moiety of formula (A), wherein the halogen (X) is independently chosen from Br, Cl, and I;

(ii) substituting a first β' or β" halogen (X) with an alkylthio group (—$SR_3$), (iii) halogenating the thiophene moiety at an α' or α" position adjacent the alkylthio group with a halogen (X') chosen from Br, Cl, and I;
(iv) substituting the α' or α" halogen (X') with an aldehyde group (—C(O)H); and
(v) substituting a second β' or β" halogen (X) with an $R_1$ group.

6. A method for making the thiophene compound of formula (I') according to claim 1, comprising:
(i) providing a β'-β"-halogen-substituted thiophene moiety of formula (A'), wherein the halogen (X) is independently chosen from Br, Cl, and I;

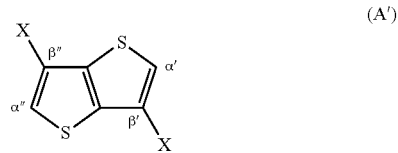

(ii) substituting a first β' or β" halogen (X) with an alkylthio group (—SR₃),
(iii) halogenating the thiophene moiety at an α' or α" position adjacent the alkylthio group with a halogen (X') chosen from Br, Cl, and I;
(iv) substituting the α' or α" halogen (X') with an aldehyde group (—C(O)H); and
(v) substituting a second β' or β" halogen (X) with an R₂ group.

7. A method for making the thiophene compound of formula (II) according to claim 1, comprising:
(i) providing a β'-β"-halogen-substituted thiophene moiety of formula (A), wherein the halogen (X) is independently chosen from Br, Cl, and I;

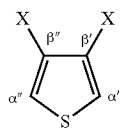
(A)

(ii) substituting the β' and β" halogens (X) with alkylthio groups (—SR₃),
(iii) halogenating the thiophene moiety at the α' and α" positions with a halogen (X') independently chosen from Br, Cl, and I;
(iv) substituting the α' and α" halogens (X') with aldehyde groups (—C(O)H);
(v) reducing the α' and α" aldehyde groups (—C(O)H) to alcohol groups (—CH₂OH),
(vi) substituting the hydroxyl group (—OH) of the α' and α" alcohol groups with a halogen (X") chosen from Br, Cl, and I; and
(vii) reacting the compound formed in step (vi) with tributylphosphine (PBu₃) or triphenyl phosphine (PPh₃).

8. A method for making the thiophene compound of formula (II') according to claim 1, comprising:
(i) providing a β'-β"-halogen-substituted thiophene moiety of formula (A'), wherein the halogen (X) is independently chosen from Br, Cl, and I;

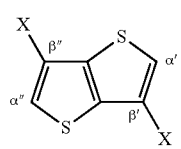
(A')

(ii) substituting the β' and β" halogens (X) with alkylthio groups(—SR₃),
(iii) halogenating the thiophene moiety at the α' and α" positions with a halogen (X') independently chosen from Br, Cl, and I;
(iv) substituting the α' and α" halogens (X') with aldehyde groups (—C(O)H);
(v) reducing the α' and α" aldehyde groups (—C(O)H) to alcohol groups (—CH₂OH);
(vi) substituting the hydroxyl group (—OH) of the α' and α" alcohol groups with a halogen (X") chosen from Br, Cl, and I; and
(vii) reacting the compound formed in step (vi) with tributylphosphine (PBu₃) or triphenyl phosphine (PPh₃).

9. A method for making the thiophene compound of formula (II") according to claim 1, comprising:
(i) providing a compound of formula (I*):

(I*)

(ii) reducing the aldehyde group (—C(O)H) to an alcohol group (—CH₂OH);
(iii) substituting the hydroxyl group (—OH) of the alcohol group with a halogen (X) chosen from Br, Cl, and I; and
(iv) reacting the compound formed in step (vi) with tributylphosphine (PBu₃) or triphenyl phosphine (PPh₃).

10. A method for making the thiophene compound of formula (II'") according to claim 1, comprising:
providing a compound of formula (I'*):

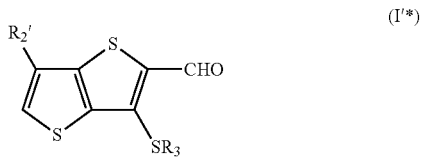
(I'*)

(ii) reducing the aldehyde group (—C(O)H) to an alcohol group (—CH₂OH);
(iii) substituting the hydroxyl group (—OH) of the alcohol group with a halogen (X) chosen from Br, Cl, and I; and
(iv) reacting the compound formed in step (vi) with tributylphosphine (PBu₃) or triphenyl phosphine (PPh₃).

11. A method for making a 13-R-substituted fused thiophene compound comprising:
(i) coupling two compounds of formula (I) or two compounds of formula (I'):

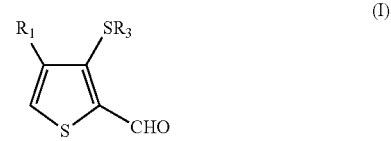
(I)

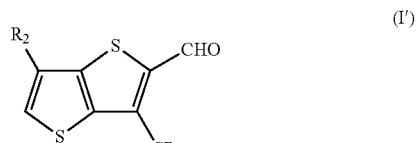
(I')

to form a compound of formula (III) or (III'):

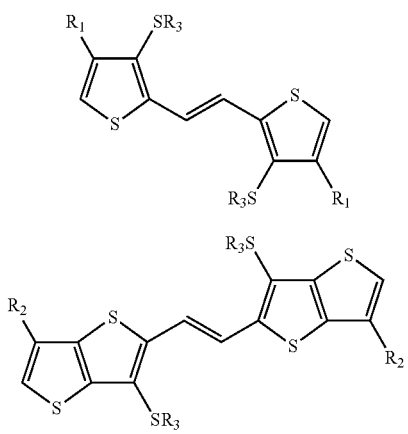

(III)

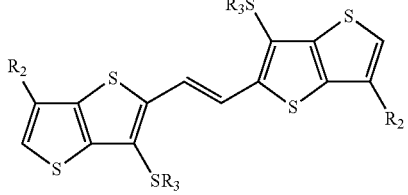

(III')

(ii) cyclizing the compound of formula (III) or (III') to form a compound of formula (IV) or (IV'):

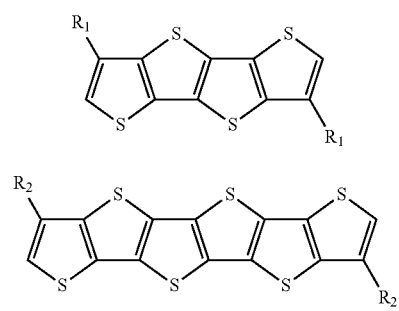

(IV)

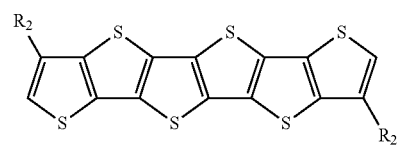

(IV')

wherein $R_1$ and $R_2$ are identical, comprise at least four carbon atoms, and are chosen from alkyl, alkenyl, alkynyl, aryl, cycloalkyl, or aralkyl groups, which can be substituted or unsubstituted, linear or branched, and optionally interrupted by at least one heteroatom; and $R_2$ are identical and are chosen from alkyl, alkenyl, alkynyl, aryl, cycloalkyl, or aralkyl groups, which can be substituted or unsubstituted, linear or branched, and optionally interrupted by at least one heteroatom.

12. The method of claim 11, wherein $R_1$ and $R_2$ are independently chosen from $C_1$-$C_{36}$ linear alkyl groups and $C_3$-$C_{48}$ branched alkyl groups.

13. The method of claim 11, wherein $R_1$ and $R_2$ are substituted with at least one group chosen from alkyl, alkenyl, alkynyl, aryl, cycloalkyl, aralkyl, ether, hydroxyl, alkoxy, thiol, thioalkyl, and halide groups.

14. A method for making a β-R-substituted fused thiophene compound comprising:

coupling a first compound chosen from compounds of formulae (I) and (I'):

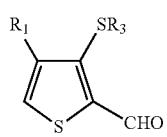

(I)

-continued

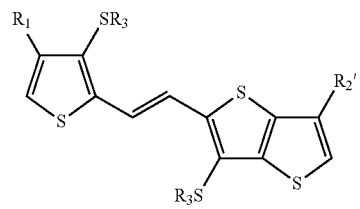

(I')

with a second compound chosen from compounds of formula (II'') or (II'''):

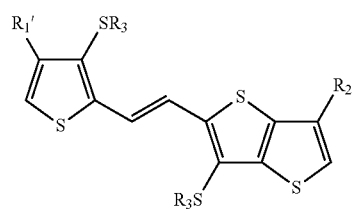

(II'')

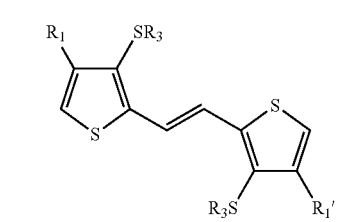

(II''')

to form a third compound of formula (III''), (III'''), (V), or (V'):

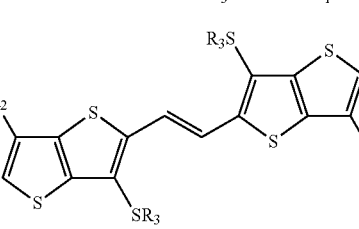

(III'')

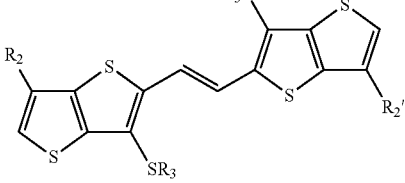

(III''')

(V)

(V')

(ii) cyclizing the compound of formula (III″), (III‴), (V), or (V′) to form a compound of formula (IV″), (IV‴), (VI), or (VI′):

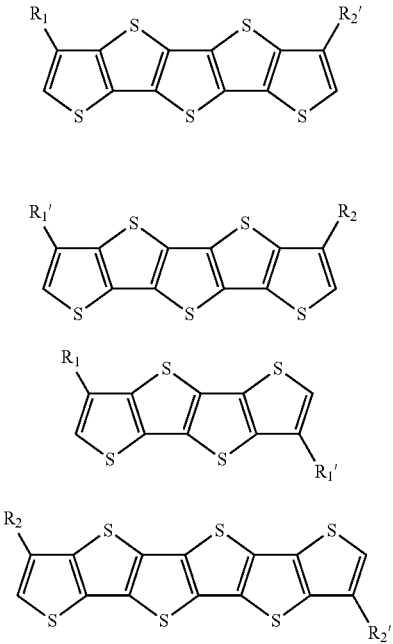

wherein $R_1$, $R_1'$, $R_2$, and $R_2'$ are identical or different and are independently chosen from alkyl, alkenyl, alkynyl, aryl, cycloalkyl, or aralkyl groups, which can be substituted or unsubstituted, linear or branched, and optionally interrupted by at least one heteroatom, and wherein at least one of $R_1$, $R_1'$, $R_2$, or $R_2'$ comprises at least four carbon atoms; $R_3$ is chosen from $C_1$-$C_6$ linear alkyl radicals; Y is chosen from butyl and phenyl groups; and $X^-$ is chosen from halogen ions.

15. The method of claim 14, wherein $R_1$, $R_1'$, $R_2$, and $R_2'$ are independently chosen from $C_1$-$C_{36}$ linear alkyl groups and $C_3$-$C_{48}$ branched alkyl groups.

16. The method of claim 14, wherein at least one of $R_1$, $R_1'$, $R_2$, or $R_2'$ is substituted with at least one group chosen from alkyl, alkenyl, alkynyl, aryl, cycloalkyl, aralkyl, ether, hydroxyl, alkoxy, thiol, thioalkyl, and halide groups.

17. The method of claim 14, wherein Y is a butyl group and $X^-$ is a bromine ion.

18. A method for making a β-R-substituted fused thiophene compound comprising:
(i) coupling a first compound chosen from compounds of formulae (I) and (I′):

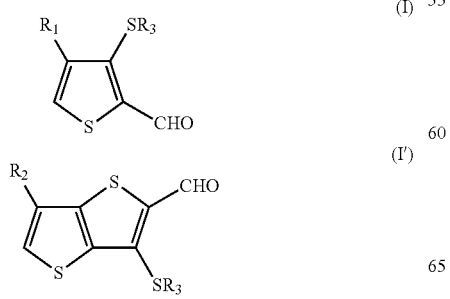

with a second compound chosen from compounds of formulae (II) or (II′):

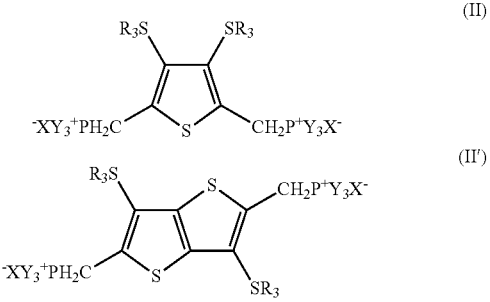

to form a third compound of formula (VII), (VII′), (VII″), or (VII‴):

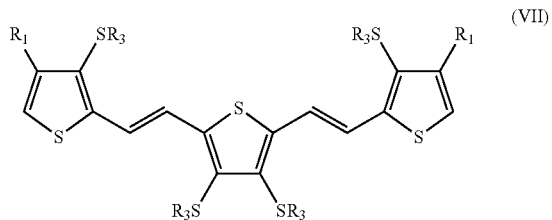

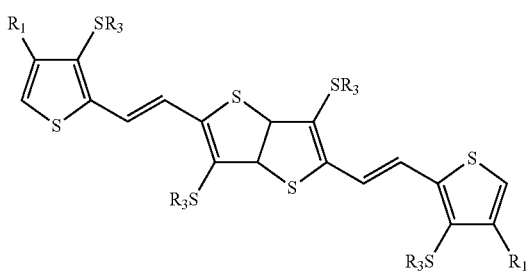

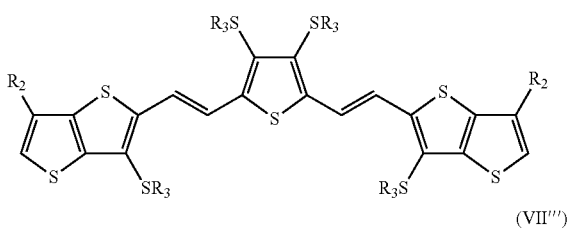

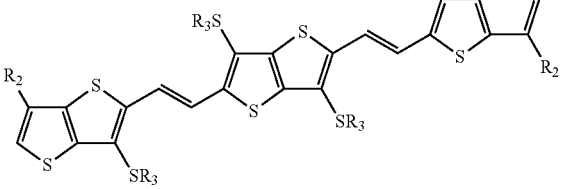

(ii) cyclizing the compound of formula (VII), (VII'), (VII''), or (VII''') to form a compound of formula (VIII), (VIII'), (VIII''), or (VIII'''):

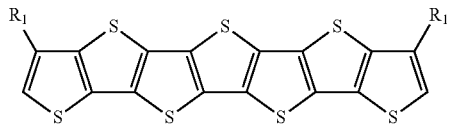
(VIII)

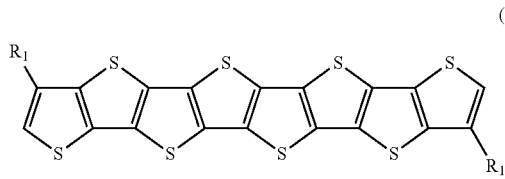
(VIII')

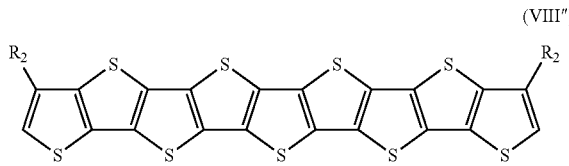
(VIII'')

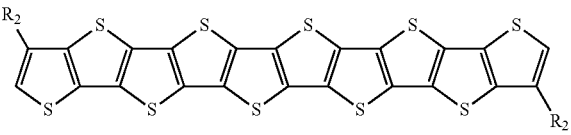
(VIII''')

wherein $R_1$ and $R_2$ are identical, comprise at least four carbon atoms, and are chosen from alkyl, alkenyl, alkynyl, aryl, cycloalkyl, or aralkyl groups, which can be substituted or unsubstituted, linear or branched, and optionally interrupted by at least one heteroatom; $R_2$ are identical and are chosen from alkyl, alkenyl, alkynyl, aryl, cycloalkyl, or aralkyl groups, which can be substituted or unsubstituted, linear or branched, and optionally interrupted by at least one heteroatom; $R_3$ is chosen from $C_1$-$C_6$ linear alkyl radicals; Y is chosen from butyl and phenyl groups; and $X^-$ is chosen from halogen ions.

19. The method of claim 18, wherein $R_1$ and $R_2$ are independently chosen from $C_1$-$C_{36}$ linear alkyl groups and $C_3$-$C_{48}$ branched alkyl groups.

20. The method of claim 18, wherein $R_1$ and $R_2$ are substituted with at least one group chosen from alkyl, alkenyl, alkynyl, aryl, cycloalkyl, aralkyl, ether, hydroxyl, alkoxy, thiol, thioalkyl, and halide groups.

21. The method of claim 18, wherein Y is a butyl group and $X^-$ is a bromine ion.

* * * * *